United States Patent [19]

Healy et al.

[11] 4,031,151

[45] June 21, 1977

[54] SEPARATION OF HYDROCARBONS

[75] Inventors: Frank J. Healy, Morristown; Paul R. Geissler, Edison, both of N.J.

[73] Assignee: Exxon Research and Engineering Company, Linden, N.J.

[22] Filed: May 12, 1976

[21] Appl. No.: 685,459

Related U.S. Application Data

[63] Continuation-in-part of Ser. No. 556,432, March 7, 1975, abandoned, which is a continuation-in-part of Ser. No. 457,056, April 1, 1974, abandoned.

[52] U.S. Cl. .................. 260/666 A; 208/310 Z; 210/31 C; 260/668 R; 260/669 A; 260/674 SA; 260/676 MS; 260/677 A; 260/681.5 R

[51] Int. Cl.² .................. C07C 7/13; C10G 25/04; B01D 15/08

[58] Field of Search ............ 260/676 MS, 666 SA, 260/668 R, 669 A, 677 A, 681.5 R; 208/310 Z; 210/31 C

[56] References Cited

UNITED STATES PATENTS

| | | | |
|---|---|---|---|
| 3,201,491 | 8/1965 | Stine et al. | 260/676 MS |
| 3,455,815 | 7/1969 | Fickel | 208/310 |
| 3,696,107 | 10/1972 | Neuzil | 260/674 SA |
| 3,715,409 | 2/1973 | Broughton | 260/674 SA |
| 3,732,325 | 5/1973 | Pharis et al. | 260/674 SA |
| 3,733,261 | 5/1973 | Adams et al. | 208/310 |
| 3,734,974 | 5/1973 | Neuzil | 260/674 SA |
| 3,761,533 | 9/1973 | Otani et al. | 260/674 SA |
| 3,843,518 | 10/1974 | Magee et al. | 210/31 C |
| 3,845,151 | 10/1974 | Priegnitz | 260/675.5 |
| 3,882,184 | 5/1975 | Rosback | 260/675.5 |

*Primary Examiner*—Delbert E. Gantz
*Assistant Examiner*—G. E. Schmitkons
*Attorney, Agent, or Firm*—C. Leon Kim

[57] ABSTRACT

Dual desorbent composition and dual temperature techniques as improvements for simulated moving-bed adsorption-desorption separation processes whereby certain hydrocarbons can be separated from mixtures containing various unsaturated and/or saturated aliphatic and/or aromatic hydrocarbons. The dual desorbent composition technique is implemented by employing a strong desorbent stream in the desorption zone and a weaker desorbent stream in the rectification zone of a simulated moving-bed countercurrent adsorption-separation system; while the dual temperature concept envisions the temperature differentiation between the desorption zone and the remaining zones of said separation system in order to both minimize the desorbent requirement and enhance the purity of the separation products. A combined use of both the dual desorbent composition and the dual temperature techniques can further improve the performance of said simulated moving-bed system.

35 Claims, 3 Drawing Figures

DUAL DESORBENT COMPOSITION

DUAL TEMPERATURE

DUAL TEMPERATURE - COMPOSITION

SEPARATION OF HYDROCARBONS

CROSS-REFERENCE TO RELATED APPLICATIONS

This application is a continuation-in-part of Ser. No. 556,432, filed Mar. 7, 1975, which is in turn a continuation-in-part of application Ser. No. 457,056, filed Apr. 1, 1974, both now abandoned.

BACKGROUND OF THE INVENTION

1. Field of the Invention

The present invention relates to improvements for separation processes which utilize simulated countercurrent flow systems wherein fluid streams flow through serially and circularly interconnected desorption, rectification and sorption zones. In particular, it pertains to improvements in separation performance of a simulated moving-bed adsorption-separation process which is used to separate certain hydrocarbons from unsaturated hydrocarbons and also from saturated hydrocarbons by employing the dual desorbent composition and/or the dual temperature technique disclosed herein.

2. Description of the Prior Art

The present process employing the above techniques is an improvement of the simulated countercurrent flow processes described in U.S. Pat. No. 3,761,533 and U.S. Pat. No. 3,201,491. In the so-called simulated countercurrent flow system, the adsorption separation column is generally divided into three (or four equivalent) zones: a sorption zone, (a primary rectification zone,) a desorption zone and a (secondary) rectification zone. A downstream portion of the sorption zone is sometimes called a primary rectification zone. These zones are serially inter-connected in order and a continuously circulated fluid stream flowing through the three (or four) zones is maintained by circulating the effluent fluid from an outlet of the last zone to an inlet of the first zone; all the points of introducing and withdrawing the inlet and outlet streams are simultaneously shifted, at stated intervals of time, in a downstream direction to thereby provide a simulated countercurrent flow system wherein there is achieved a processing effect similar to that observed in a moving-bed type adsorption process. In such a process, at least one of the components of the liquid feedmixture is selectively sorbed by contact with solid sorbent particles; said liquid feed mixture is allowed to flow through the three serially and circularly interconnected zones, i.e., the desorption, the rectification and the sorption zones, each zone being divided into a plurality of serially interconnected sections, each section being packed with a mass of solid sorbent particles; introducing a desorbent stream into the first section of the desorption zone; introducing the liquid feed mixture to the first section of the sorption zone and withdrawing a raffinate effluent comprising a less sorbed component and the desorbent from the sorption zone; and all the points of introducing and withdrawing the liquid streams into and from the sections are simultaneously shifted, at stated intervals of time, in a downstream direction, while maintaining the same order to continuity and the same spatial relationship between all the points.

In conducting the above-described process, several attempts were made to reduce the total desorbent requirements and also enhance the purity of the recovered sorbate. Stine et al., for example, disclosed a process in U.S. Pat. No. 3,201,491 (1965) which employs a portion of the desorption effluent withdrawn from the last section of the desorption zone by passing it directly into the (secondary) rectification zone in order to physically wash the raffinate materials remaining in the inactive void interstices between the active sorbent particles. An externally-prepared purging fluid comprising the sorbate and raffinate components of the feedstock was also claimed in their patent. Another improvement described in U.S. Pat. No. 3,455,815 (Fickel; 1967) envisions the employment of a stream consisting essentially of an inert material in order to flush non-selectively sorbable components of the feedstock from the interstitial void spaces between the sorbent particles in the rectification zone. A third method which is described in U.S. Pat. No. 3,761,533 (Otani et al.; 1973) introduces a portion of the desorption effluent which is rich in sorbate content into the rectification zone for the purpose of enhancing the purity of the sorbate component adsorbed within the rectification zone.

The above methods, however, contain certain deficiencies. The use of a portion of the desorption effluent will not only result in an increase in the desorbent consumption but also can desorb certain amounts of sorbate adsorbed within the rectification zone and thereby limit the overall efficiency of the system. Further, Fickel's concept of employing a flushing stream consisting essentially of an inert material may not provide an adequate means to desorb chemically-adsorbed raffinate materials; and, consequently, the purity of the sorbate product may not be satisfactory. It has now been discovered that the employment of the dual desorbent composition technique and/or the dual temperature technique described herein can substantially eliminate the above deficiencies and markedly improve the overall performance of sorption-separation processes.

SUMMARY OF THE INVENTION

In accordance with the present invention, simulated countercurrent flow adsorption-separation processes as described above are operated with the dual desorbent composition technique of the instant invention. In this inventive embodiment, two desorbent streams of different strengths are employed. The first desorbent stream, $D_1$, when employed in the desorption zone, is more strongly sorbable on the sorbent particles than the most strongly sorbable component of the feed stream, while the second desorbent stream, $D_2$, which is introduced into the rectification zone, is less sorbable than $D_1$ and is preferentially intermediate in strength between the most strongly adsorbed sorbate and the weakly adsorbed raffinate. $D_2$ may consist of the same desorbent material as $D_1$ but is made less strongly adsorbable by dilution with an inert material such as paraffin. However, the amount of the inert material employed in $D_2$ should not be higher than 90 weight percent based on the total charge of $D_2$.

In another separate embodiment of the present invention, simulated countercurrent separation processes can be also improved by the use of a temperature gradient technique. It has been discovered that, by preheating the desorbent stream to higher temperatures prior to its introduction to the desorption zone with a heat exchanger or other suitable heating means, the desorbing strength of the desorbent stream can be significantly increased. In this embodiment, therefore, higher temperatures in the desorption zone permit the use of smaller amounts of desorbent than would be required at lower temperatures. Simultaneously, in accordance with this embodiment, lower temperatures are employed in the rectification and the sorption zones to permit easy adsorption of the feed. In practicing this inventive embodiment, accordingly, there should be maintained a minimum temperature difference of butene-2 and cis- from trans-piperylene; (e) separation of $C_4$-$C_{12}$ diolefins from $C_4$-$C_{12}$ monoolefins, e.g., butadiene from butenes and n-acetylenes from isoprene; and (f) separation of $C_5$-$C_{15}$ acyclic unsaturated hydrocarbons from $C_5$-$C_{15}$ cyclic unsaturated hydrocarbons, e.g., isoprene from cyclopentadiene and isoprene from cyclopentene. In effecting these various separations, paraffinic materials

TABLE 1

REPRESENTATIVE SEPARATION SYSTEMS

| Sorbate | Raffinate | Desorbent (Diluent: $C_8$-$C_{18}$ Paraffins) | Sieve | Content of Desorbent in $D_1$, Wt.%[1] | | | Content of Desorbent in $D_2$, Wt.%[1] | | |
|---|---|---|---|---|---|---|---|---|---|
| | | | | Preferred | More Preferred | Most Preferred | Preferred | More Preferred | Most Preferred |
| $C_8$-$C_{18}$ olefins | $C_8$-$C_{18}$ paraffins | $C_8$-$C_{18}$ olefins | Groups IA, IB, IIA, IIB zeolites: e.g., NaX,NaY,CuX, CuY,CdX,CdY, SrX,SrY,KY | 40–100 (0–60) | 50–90 (10–50) | 60–75 (25–40) | 15–60 (40–85) | 20–50 (50–80) | 25–40 (60–75) |
| $C_6$-$C_{12}$ aromatics | $C_8$-$C_{18}$ olefins | $C_6$-$C_{14}$ aromatics | Group IA zeolites:e.g., NaX,KY,LiY | 30–100 (0–70) | 50–85 (15–50) | 60–75 (25–40) | 10–50 (50–90) | 20–45 (55–80) | 25–40 (60–75) |
| $C_4$-$C_{12}$ normal olefins | $C_4$-$C_{12}$ branched olefins | $C_1$-$C_8$ alkanols | Group IA Zeolites:e.g., KX,KY,BaX,BaY | 50–100 (0–50) | 60–90 (10–40) | 70–80 (20–30) | 15–50 (50–85) | 20–40 (60–80) | 25–35 (65–75) |
| $C_4$-$C_8$ cis-olefins | $C_4$-$C_8$ trans-olefins | $C_8$-$C_{18}$ olefins | Groups IB and IIB zeolites:e.g., CuX,CuY,ZnY,ZnX | 40–100 (0–60) | 50–90 (10–50) | 60–75 (25–40) | 15–60 (40–85) | 20–50 (50–80) | 25–40 (60–75) |
| $C_4$-$C_{12}$ diolefins | $C_4$-$C_{12}$ monoolefins | $C_4$-$C_{12}$ diolefins | Group IA zeolites:e.g., NaX, NaY | 40–100 (0–60) | 50–85 (15–50) | 60–75 (25–40) | 15–60 (40–85) | 20–45 (55–80) | 30–40 (60–70) |
| $C_5$-$C_{15}$ acyclic unsaturated hydrocarbons | $C_5$-$C_{15}$ cyclic unsaturated hydrocarbons | $C_6$-$C_{10}$ aromatics | Groups IA & IIA zeolites: e.g., CaX, KY | 30–100 (0–70) | 40–90 (10–60) | 50–80 (20–50) | 15–40 (60–85) | 20–35 (65–80) | 25–30 (70–75) |

NOTE:
[1] Parenthesized numericals indicate the fractions of $C_8$-$C_{18}$ paraffinic diluents in $D_1$ and $D_2$.

about 5° C. between the heated desorbent stream and the operating temperatures of the rectification and sorption zones.

In further embodiment, the simulated countercurrent flow separation process may be operated by combining both the dual desorbent composition and the dual temperature techniques. This embodiment utilizes a weaker desorbent $D_2$ in the rectification zone and a stronger desorbent $D_1$ in the desorption zone, with $D_1$ being at a higher temperature than $D_2$. The result of the combination would be a much greater saving in the desorbent requirements and, accordingly, in greater reduction in cost than either of the embodiments effected separately.

In this specification, diluent or inert material is taken as liquid materials which are not significantly adsorbed by the sorbent substrate in the presence of feedmixture components. Eluent or desorbent is a term to describe the liquid materials which are adsorbed by the substrate and compete for adsorption sites with the feed components. The substance employed as the desorbent is generally a material capable of displacing sorbate component of the feedstock already adsorbed on the solid sorbent when the beds now comprising the desorption zone were in the rectification zone of a previous cycle of operation.

As shown in Table I, the instant inventive concept is applicable to a wide variety of separations: for example, (a) separation of $C_8$-$C_{18}$ olefins from $C_8$-$C_{18}$ paraffins, e.g., butene-2 from butane; (b) separation of $C_6$-$C_{12}$ aromatics from $C_8$-$C_{16}$ olefins, e.g., benzene from octenes; (c) separation of $C_4$-$C_{12}$ n-olefins from $C_4$-$C_{12}$ branched olefins, e.g., butene-1 from isobutylene and piperylene from isoprene; (d) separation of $C_4$-$C_8$ cis-olefins from $C_4$-$C_8$ trans-olefins, e.g., cis-from transhaving from 8 to 18 carbon atoms may be commonly employed as the diluent in formulating the strong desorbent stream ($D_1$) and the weak desorbent stream ($D_2$). However, the desorbent materials to be employed may vary with the hydrocarbon feedmixtures to be separated. For example, as summarized in Table I, $C_8$-$C_{18}$ olefins may be employed as the desorbent for separating $C_8$-$C_{18}$ olefins from $C_8$-$C_{18}$ paraffins; $C_6$-$C_{14}$ aromatics for separating $C_6$-$C_{12}$ aromatics from $C_8$-$C_{16}$ olefins; $C_1$-$C_8$ alkanols for separating $C_4$-$C_{12}$ n-olefins from $C_4$-$C_{12}$ branched olefins; $C_8$-$C_{18}$ olefins for separating $C_4$-$C_8$ cis-olefins from $C_4$-$C_8$ transolefins; $C_4$-$C_{12}$ diolefins for separating $C_4$-$C_{12}$ diolefins from $C_4$-$C_{12}$ monoolefins; and $C_6$-$C_{10}$ aromatics for separating $C_5$-$C_{15}$ acyclic unsaturated hydrocarbons from $C_5$-$C_{15}$ cyclic unsaturated hydrocarbons. While Table I is intended to illustrate various separation systems amenable to the utilization of the dual desorbent composition technique, employed either alone or in combination with the dual temperature technique, the same separation systems, i.e., the same sorbent sieves, feedmixtures, desorbent materials as enumerated in Table I as well as the common $C_8$-$C_{18}$ paraffinic diluents, are also amenable to the application of a single desorbent stream embodying the dual temperature concept. Thus, when the single desorbent stream is employed for the practice of the dual temperature technique, the desorbent stream may comprise, depending upon the characteristics of the feedmixtures, one of the suitable desorbents listed in Table I in an amount within the range of from about 10 to about 100 wt. %, preferably from about 20 to 80 wt. %, and more preferably from about 30 to 70 wt. % based on the total charge of the desorbent stream. Although the concentrations of desorbent materials for $D_1$ and $D_2$ employed in utilizing the inventive embodiment of dual desorbent composition, as shown in Table I, may sometimes appear to be overlapping, it should be understood that the concentration of the desorbent material present in $D_1$ is always higher than that of the desorbent material present in $D_2$ at least by 20 wt. %. Further, the volume ratio of the strong desorbent stream $D_1$ to the weak desorbent stream $D_2$ is generally in the range of from about 4/1 to about 1/3, preferably from about 3/1 to about ½, and more preferably from about 2/1 to about 1/1.

In carrying out one or more of the above-described separations, it is found that the following process conditions are applicable. While the applicable temperature and pressure ranges vary widely depending on the materials being separated, temperatures, when the dual desorbent composition embodiment is being employed, will generally be in the range of from −50° to 500° C., preferably from 0° to 300° C., and more preferably from 25° to 200° C. Pressures will range from 0.1 to 100 atm., preferably from 1 to 40 atm., and more preferably from 1 to 20 atm. The above temperature ranges are broad since the operating range used in any given system depends on the boiling temperatures of the components of the mixtures being separated. In separating low boiling feed mixtures, a lower temperature range will be used than in separating higher boiling feed mixtures. When the dual temperature technique with a single desorbent stream is employed, the temperature of the desorbent stream introduced into the desorption zone should be higher than that of the streams flowing into the rectification and sorption zones by at least 5° C. The upper limit of the temperature difference is normally controlled by various operating factors such as the critical temperatures at which some of the materials employed begin to pyrolyze or isomerize. This instant invention and its embodiments are further explained below with reference to FIGS. 1, 2 and 3.

DESCRIPTION OF THE PREFERRED EMBODIMENTS

Figure 1:
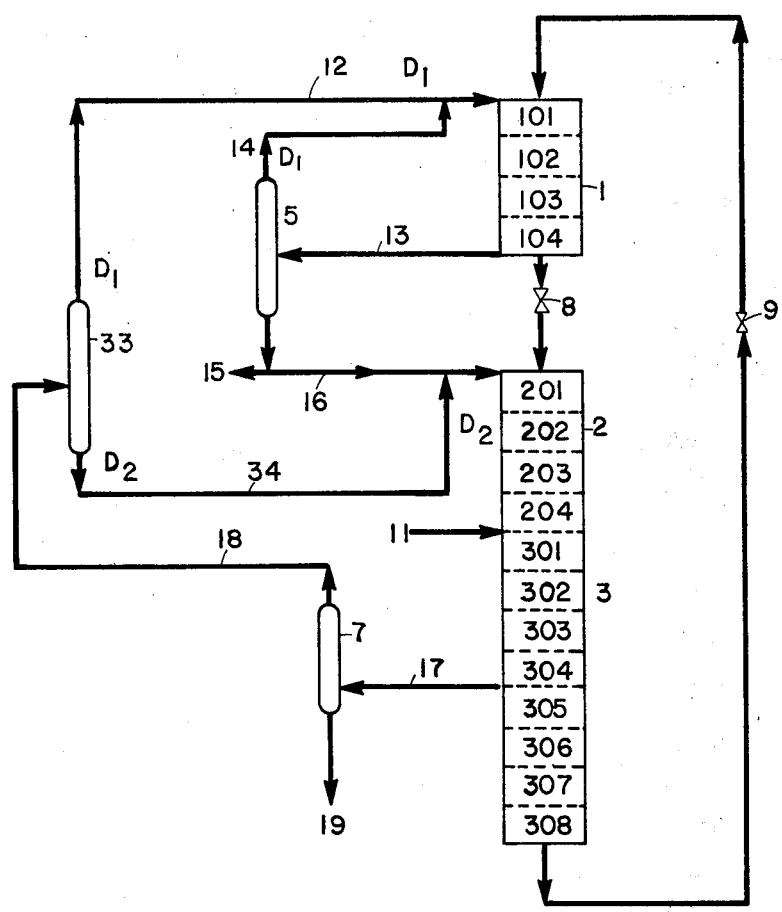
FIG. 1 represents a simplified version of a simulated moving-bed countercurrent separation system which employs two desorbent streams of different strengths: the stronger desorbent stream in the desorption zone and the weaker desorbent stream in the rectification zone.
Figure 2:
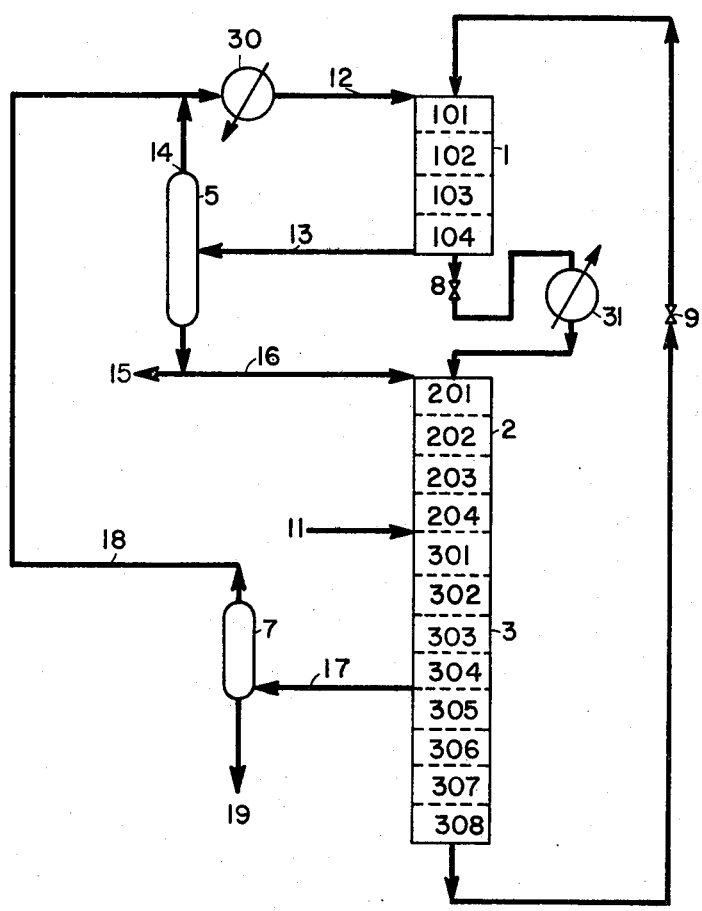
FIG. 2 shows a simulated moving-bed system which employs the desorbent stream with higher temperature in the desorption zone.
Figure 3:
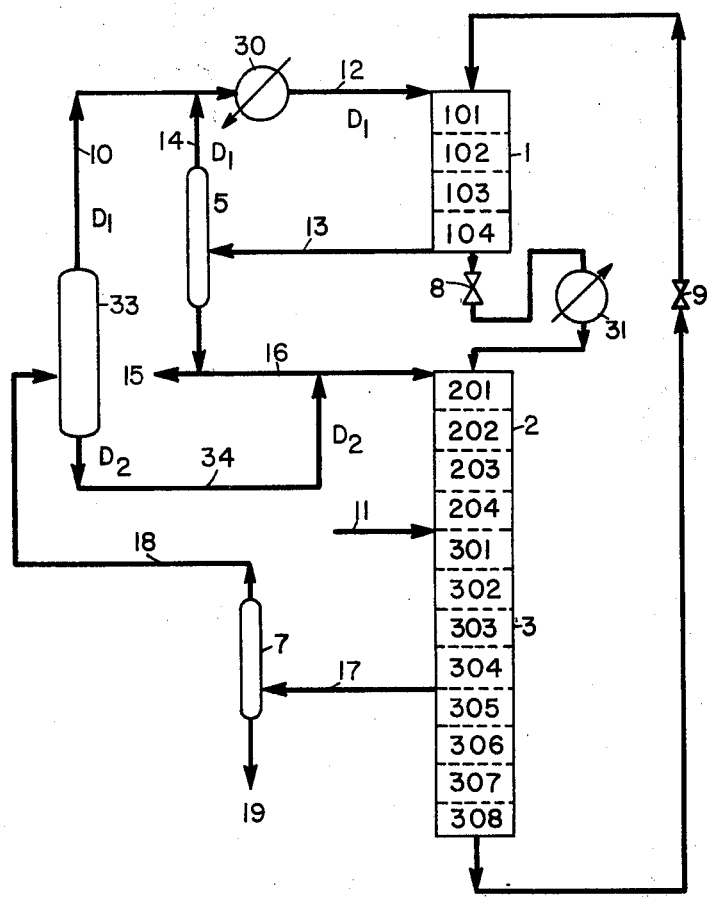
FIG. 3 illustrates a simulated moving-bed system which combines the dual desorbent composition and the dual temperature techniques in order to markedly enhance the separation efficiency of the system.

The simulated moving-bed sorption-desorption systems illustrated in FIGS. 1, 2 and 3 are assumed to be under their steady-state operating conditions; and, consequently, it is assumed that no fresh feeds of the desorbent materials need be added as the desorbent streams with chosen concentrations will be constantly reconstituted and recycled within the systems. As shown in FIG. 1, the stronger desorbent stream $D_1$ flows into the first section 101 of the desorption zone 1 through line 12 which is joined by line 14. It should be noted that this desorption zone, in the previous cycle of operation, functioned as the rectification zone 2; and that only the desired sorbate component has been selectively retained and sorbed onto the solid sorbent particles charged in the desorption zone. This selectively retained sorbate is desorbed by the stronger desorbent stream 12 within the desorption zone 1; and the mixture comprising the eluted sorbate and the desorbent, which mixture will be called the desorption effluent, is withdrawn through an outlet of the last section 104 of the desorption zone 1. All or a major portion of this desorption effluent is then sent through line 13 to a distillation column 5 where the desorption effluent is separated into the desorbent stream 14 which is recycled to the desorption zone and the sorbate-product stream. To facilitate this separation of the desorbent mixture from the sorbate product in distillation column 5, therefore, the desorbent and the diluent employed are such that their boiling points are substantially higher or lower than the boiling point of the sorbate component. All or a major portion of the sorbate product so separated is withdrawn from the system as the final product 15; and the remaining minor portion 16 may be optionally sent to the top section 201 of the rectification zone 2 as a reflux stream. A minor portion of the desorption effluent may also be optionally routed to the rectification zone 2 through a valve 8. The weaker desorbent stream $D_2$ which is reconstituted in distillation column 33 is introduced, through line 34 joining line 16, into the top section 201 of the rectification zone 2 in order to effect the desorption of the weakly-sorbed raffinate so that, when this rectification zone becomes a desorption zone in the succeeding cycle of operation, only the desired sorbate component may remain adsorbed on the sorbent substrate in a quality of high purity. A liquid feed mixture 11 comprising at least a sorbate component and a raffinate component is injected into the top section 301 of the sorption zone 3. In the sorption zone 3, the feed flow joined by the effluent from the rectification zone (not shown) is countercurrently contacted with the simulated upward flow of the solid sorbent particles, resulting in the adsorption of the selectively sorbable component of the feedstream onto the sorbent particles. The mixture of the desorbent and less sorbable raffinate materials which have lost sorption sites to more strongly sorbed molecules is then withdrawn from an outlet point positioned between sections 304 and 305 of the sorption zone 3 through line 17. This raffinate effluent is then sent to distillation column 7 wherein the raffinate effluent is separated into the desorbent stream 18 and the raffinate product 19.

In typical operations, the entire liquid stream flowing through the sorption zone 3 is divided into two portions: one portion being withdrawn from zone 3 as a raffinate effluent 17 and the other portion being allowed to flow directly down into the remaining sections 305, 306, 307, 308. These remaining sections are sometimes called a primary rectification zone. The number of the sections existing downstream from the withdrawal point of raffinate effluent 17 in the sorption zone 3 is determined in such a manner that the concentration of the raffinate contained in the stream flowing down through these sections reaches approximately zero at the bottom of the last section 308. Thus, the stream substantially free of the raffinate component is directly and continuously introduced through a valve 9 into the desorption zone 1.

The sorption zone 3 may also be operated without the downstream sections 305, 306, 309 and 308. In this embodiment of operation, all or a major portion of the raffinate effluent 17 is withdrawn from the last section 304 of the sorption zone; and a minor portion of the raffinate effluent may be optionally routed, through valve 9, into the top section 101 of the desorption zone 1.

In general, the desorbent stream 18 recovered from distillation column 7 has a higher concentration than that of $D_2$, due to the influx of, in addition to the weaker desorbent stream $D_2$, an optional amount of the stronger desorbent stream $D_1$ from the desorption zone 1 through valve 8 into the rectification and the sorption zone 2, 3 and also due to the presence of the strong desorbent material desorbed from the sorbent particles charged within the sorption zone 3. This strong desorbent material eluted in the sorption zone 3 is the fraction which has stayed adsorbed onto the sorbent substrate from the previous cycle when the sorption zone 3 functioned as the desorption zone 1. In order to reconstitute the weaker desorbent stream $D_2$, therefore, the desorbent stream 18 from distillation column 7 is further treated in distillation column 33. If two different desorbing materials or eluents are employed, the eluent with stronger desorbing ability can be recovered, for example, as the tops product and the weaker desorbing material as the bottoms product. If an identical desorbent material and a common diluent are used, the concentrations of the inert material in the bottoms and the tops product streams can be controlled so as to obtain the two $D_1$ and $D_2$ streams with their desired strengths.

The dual temperature embodiment may be more readily understood with reference to FIG. 2 which shows the desorbent stream being heated prior to its introduction to desorption zone 1 with a heat exchanger 30 or by other suitable means known to the art; and removing the residual heat, through the use of heat exchanger 31, before a portion of the desorption effluent passes into the rectification zone. Normally, the separation system is operated isothermally (except the desorption zone in this embodiment); and the temperature difference between the heated desorbent stream 12 and other streams going into the rectification zone should be maintained at least above 5° C. It should be understood that the temperature of the reflux stream 16 has been adjusted, through the use of suitable means, e.g., a heat exchanger (not shown), so that the rectification zone can be maintained at a substantially isothermal condition. Flow sequence in FIG. 2 is otherwise identical to that described above for FIG. 1, except that distillation column 33 and associated stream 34 have been deleted.

Other applicable schemes for this embodiment include the utilization of distillation column 5 and 7 in such a way to produce stream 12 at a sufficiently high temperature; and also heating of the desorption zone by means of a heating medium other than the desorbent stream, e.g., electric heating tapes, thereby eliminating the need for employing heat exchanger 30. Additionally, heat exchanger 31 may be eliminated if the heat capacity of desorption zone 1 is large enough to adequately cool the desorption effluent, a portion of which passing through valve 8.

The embodiment which combines both the dual temperature and the dual composition concepts may be more readily understood with reference to FIG. 3 which shows the strong desorbent stream (stream 10 from distillation column 33 and stream 14 from distillation column 5) being heated prior to its introduction to desorption zone 1 with a heat exchanger 30. Weak desorbent stream 34 flows into the first section 201 of the rectification zone 2, along with an optional amount of reflux stream 16. Stream 34 is weaker in desorbability than stream 12 by virtue of both its lower temperature and its lower concentration of diluent in its desorbent-diluent composition. Again, the temperatures of all the streams flowing into and leaving from the system, except the desorption zone in this embodiment, are assumed to be maintained substantially identical through the use of suitable means, e.g., a heat exchanger (not shown in FIG. 3), known to the art. Although it is not always necessary to maintain a minimum temperature difference between streams 12 and 34 in this embodiment combining the dual desorbent composition and the dual temperature techniques, a higher temperature gradient is more desirable as it entails a higher efficiency. A minor portion of the desorption effluent from the last section 104 of the desorption zone may be optionally sent to the rectification zone after its temperature is adjusted to a temperature compatible to that of the rectification zone through the use of heat exchanger 31. Flow sequence in FIG. 3 is otherwise identical to that described above for FIG. 1.

The process of the present invention is further illustrated by the following examples. These examples, being in the present tense, should be taken as a set of guidelines demonstrating how to work the inventive embodiments and the efficacy of the invention; but not as an account of acts actually carried out.

EXAMPLES 1 THROUGH 10

The process as shown in FIG. 1 utilizing distillation column 33 to supply a strong desorbent stream 12 and a weak desorbent stream 34 is separately operated with several sieves for separating the feed mixtures 11 of various compositions at different temperatures. The resulting improved volume ratios of the desorbent streams 14 to the sorbate product 15 are also shown in Table II.

TABLE II

| Ex. No. | Feed Mixture | Sieve | T° C | Strong Desorbent, Wt. % | | Weak Desorbent, Wt. % | | Product | Ratio (Desorbent/Product) |
|---|---|---|---|---|---|---|---|---|---|
| | | | | Eluent | Inert | Eluent | Inert | | |
| 1 | Butene-1, Butene-2, isobutylene | KY | −25 | 80 Octene | 20 Octane | 40 Octene | 60 Octane | Butene-1 | 7 |
| 2 | Butene-2, Butane | CuY | −25 | 90 Octene | 10 Octane | 30 Octene | 70 Octane | Butene-2 | 6 |
| 3 | Cis-Butene-2, trans-butene-2 | ZnX | −25 | 75 Octene | 25 Octane | 25 Octene | 75 Octane | cis Butene-2 | 8 |
| 4 | n-pentene, isopentene | KY | −15 | 80 Decene | 20 Decane | 40 Decene | 60 Decane | n-pentene | 7 |
| 5 | Octene-1, Octene-3 | $(NH_3)$Y | 25 | 75 Dodecene | 25 Dodecane | 25 Dodecene | 75 Dodecane | Octene-1 | 5 |
| 6 | Butene-2, butane | CdX | −25 | 90 Octene | 10 Octane | 30 Octene | 70 Octane | Butene-2 | 6 |
| 7 | Isoprene, α-acetylene | NaY | −15 | 75 Methanol | 25 Octane | 20 Methanol | 80 Octane | Isoprene | 7 |

TABLE II-continued

| Ex. No. | Feed Mixture | Sieve | T° C | Strong Desorbent, Wt. % Eluent | Strong Desorbent, Wt. % Inert | Weak Desorbent, Wt. % Eluent | Weak Desorbent, Wt. % Inert | Product | Ratio (Desorbent/ Product) |
|---|---|---|---|---|---|---|---|---|---|
| 8 | Piperylene, isoprene | KX | −15 | 85 Octene | 15 Octane | 35 Octene | 65 Octane | Piperylene | 6 |
| 9 | Isoprene, cyclo-pentene | KY | −25 | 80 Decene | 20 Decane | 33 Decene | 67 Decane | Isoprene | 7 |
| 10 | Cetene, cetane | KY | 100 | 80 Octene | 20 Octane | 30 Octene | 70 Octane | Cetene | 8 |

EXAMPLES 11 THROUGH 20

The process as shown in FIG. 2 utilizing a heater 30 to preheat desorbent stream 12 to a temperature 30° C. higher than the desorbent temperature is section 201 is separately operated with the same sieves, temperatures and feedmixtures as in Examples 1 through 10. It is found that the volume ratios of the desorbent stream 14 to the product stream 15 are as shown in Table III.

TABLE III

| Example No. | Feed Mixture | Sieve | T° C. | Desorbent, Wt. % Eluent | Desorbent, Wt. % Inert | Product | Ratio (Desorbent/ Product) |
|---|---|---|---|---|---|---|---|
| 11 | Butene-1, Butene-2, iso-butylene | KY | −25 | 40 Octene | 60 Octane | Butene-1 | 9 |
| 12 | Butene-2, Butane | CuY | −25 | 30 Octene | 70 Octane | Butene-2 | 8 |
| 13 | Cis-Butene-2, trans-butene-2 | ZnX | −25 | 25 Octene | 75 Octane | Cis-Butene-2 | 9 |
| 14 | n-pentene, isopentene | KY | −15 | 40 Decene | 60 Decane | n-pentene | 9 |
| 15 | Octene-1, Octene-3 | (NH₃)Y | 25 | 25 Do-decene | 75 Do-decane | Octene-1 | 7 |
| 16 | Butene-2, Butane | CdX | −25 | 30 Octene | 70 Octane | Butene-2 | 8 |
| 17 | Isoprene, α-acetylene | NaX | −15 | 20 Methanol | 80 Octane | Isoprene | 9 |
| 18 | Piperylene, isoprene | KX | −15 | 35 Octene | 65 Octane | Piperylene | 8 |
| 19 | Isoprene, cyclopentene | KY | −25 | 33 Decene | 67 Decane | Isoprene | 9 |
| 20 | Cetene, Cetane | KY | 100 | 30 Octene | 70 Octane | Cetene | 10 |

EXAMPLES 21 THROUGH 30

The process as shown in FIG. 3 utilizing distillation column 33 and preheater 30 to supply a high-temperature strong desorbent stream 12 and a weak desorbent stream 34 at a temperature 30° C. lower than stream 12 is separately operated with the same sieves, temperatures and feedmixtures as in Examples 1 through 10. It is found that the volume ratios of the desorbent stream 14 to the product stream 15 are as shown in Table IV.

TABLE IV

| Example No. | Feed Mixture | Sieve | T° C | Strong Desorbent, Wt. % Eluent | Strong Desorbent, Wt. % Inert | Weak Desorbent, Wt. % Eluent | Weak Desorbent, Wt. % Inert | Product | Ratio (Desorbent/ Product) |
|---|---|---|---|---|---|---|---|---|---|
| 21 | Butene-1, Butene-2, Isobutylene | KY | −25 | 80 Octene | 20 Octane | 40 Octene | 60 Octane | Butene-1 | 5 |
| 22 | Butene-2, Butane | CuY | −25 | 90 Octene | 10 Octane | 30 Octene | 70 Octane | Butene-2 | 4 |
| 23 | Cis-Butene-2, trans-Butene-2 | ZnX | −25 | 75 Octene | 25 Octane | 25 Octene | 75 Octane | Cis-Butene-2 | 5 |
| 24 | n-pentene, isopentene | KY | −15 | 80 Decene | 20 Decane | 40 Decene | 60 Decane | n-pentene | 6 |
| 25 | Octene-1, Octene-3 | (NH₃)Y | 25 | 75 Do-decene | 25 Do-decane | 25 Do-decene | 75 Do-decane | Octene-1 | 4 |
| 26 | Butene-2, Butane | CdX | −25 | 90 Octene | 10 Octane | 30 Octene | 70 Octane | Butene-2 | 4 |
| 27 | Isoprene, α-acetylene | NaX | −15 | 75 Methanol | 25 Octane | 20 Methanol | 80 Octane | Isoprene | 5 |
| 28 | Piperylene, isoprene | KX | −15 | 85 Octene | 15 Octane | 35 Octene | 65 Octane | Piperylene | 5 |
| 29 | Isoprene, cyclopentene | KY | −25 | 80 Decene | 20 Decane | 33 Decene | 67 Decane | Isoprene | 6 |
| 30 | Cetene, Cetane | KY | 100 | 80 Octene | 20 Octane | 30 Octene | 70 Octane | Cetene | 7 |

EXAMPLES 31 THROUGH 40

The procedure of Examples 11 through 20 are separately repeated except that desorbent stream 12 is not heated and is at the same temperature as desorbent stream 34. It is found that the volume ratios of the desorbent stream 14 to the product stream 15 are as shown in Table V.

TABLE V

| Example No. | Feed Mixture | Sieve | T° C | Desorbent, Wt. % Eluent | Desorbent, Wt. % Inert | Product | Ratio (Desorbent/ Product) |
|---|---|---|---|---|---|---|---|
| 31 | Butene-1, Butene-2, Isobutylene | KY | −25 | 40 Octene | 60 Octane | Butene-1 | 10 |
| 32 | Butene-2, Butane | CuY | −25 | 30 Octene | 70 Octane | Butene-2 | 9 |
| 33 | Cis-Butene-2, trans-butene-2 | ZnX | −25 | 25 Octene | 75 Octane | Cis-Butene-2 | 10 |
| 34 | n-pentene, isopentene | KY | −15 | 40 Decene | 60 Decane | n-pentene | 11 |
| 35 | Octene-1, Octene-3 | (NH₃)Y | 25 | 25 Do-decene | 75 Do-decane | Octene-1 | 8 |
| 36 | Butene-2, Butane | CdX | −25 | 30 Octene | 70 Octane | Butene-2 | 9 |
| 37 | Isoprene, α-acetylene | NaX | −15 | 20 Methanol | 80 Octane | Isoprene | 10 |
| 38 | Piperylene, isoprene | KX | −15 | 35 Octene | 65 Octane | Piperylene | 9 |

TABLE V-continued

| Example No. | Feed Mixture | Sieve | T° C | Desorbent, Wt. % | | | Ratio (Desorbent/ |
|---|---|---|---|---|---|---|---|
| | | | | Eluent | Inert | Product | Product) |
| 39 | Isoprene, cyclopentene | KY | −25 | 33 Decene | 67 Decane | Isoprene | 11 |
| 40 | Cetene, Cetane | KY | 100 | 30 Octene | 70 Octane | Cetene | 12 |

Examples 1 through 40 show that the use of stronger desorbents in desorption zone 1, wherein its strength is increased by an increase in temperature and/or an increase in eluent concentration, decreases the overall desorbent volume requirements and therefore results in a more efficient process for the separation and recovery of the desired products.

What is claimed is:

1. In a process for continuously separating, in a liquid phase, the components of a liquid hydrocarbon feedstream wherein at least one of said components is selectively adsorbed by contact with a solid sorbent utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent, the improvement which comprises:
   a. introducing a first desorbent stream containing a desorbent and a $C_8$-$C_{18}$ paraffinic diluent into the first section of said desorption zone;
   b. withdrawing a desorption effluent containing a selectively sorbed component from the last section of said desorption zone;
   c. introducing a second desorbent stream containing said paraffinic diluent and at least about 10 weight percent of said desorbent into the first section of said rectification zone;
   d. introducing said hydrocarbon feedstream into the first section of said sorption zone;
   e. withdrawing a raffinate effluent containing a less sorbed component from the last section of said sorption zone; and
   f. wherein the concentration of said desorbent present in the first desorbent stream is higher than the concentration of said desorbent present in the second desorbent stream by at least 20 weight percent.

2. The process of claim 1 wherein the first desorbent stream employed in step (a) is heated, before it is introduced into the first section of said desorption zone, to a temperature higher than the temperature of the second desorbent stream employed in step (c).

3. The process of claim 1 wherein said liquid hydrocarbon feedstream contains an olefin having from 8 to 18 carbon atoms and a paraffin having from 8 to 18 carbon atoms.

4. The process of claim 3 wherein the desorbent employed is an olefin having from 8 to 18 carbon atoms.

5. The process of claim 1 wherein said liquid hydrocarbon feedstream contains an aromatic compound having from 6 to 12 carbon atoms and an olefin having from 8 to 16 carbon atoms.

6. The process of claim 5 wherein the desorbent employed is an aromatic compound having from 6 to 14 carbon atoms.

7. The process of claim 1 wherein said liquid hydrocarbon feedstream contains a normal olefin having from 4 to 12 carbon atoms and a branched olefin having from 4 to 12 carbon atoms.

8. The process of claim 7 wherein the desorbent employed is an alkanol having from 1 to 8 carbon atoms.

9. The process of claim 1 wherein said liquid hydrocarbon feedstream contains a cis-olefin having from 4 to 8 carbon atoms and a trans-olefin having from 4 to 8 carbon atoms.

10. The process of claim 9 wherein the desorbent employed is an olefin having from 8 to 18 carbon atoms.

11. The process of claim 1 wherein said liquid hydrocarbon feedstream contains a diolefin having from 4 to 12 carbon atoms and a monoolefin having from 4 to 12 carbon atoms.

12. The process of claim 11 wherein the desorbent employed is a diolefin having from 4 to 12 carbon atoms.

13. The process of claim 1 wherein said liquid hydrocarbon feedstream contains an acyclic unsaturated hydrocarbon having from 5 to 15 carbon atoms and a cyclic unsaturated hydrocarbon having from 5 to 15 carbon atoms.

14. The process of claim 13 wherein the desorbent employed is an aromatic compound having from 6 to 10 carbon atoms.

15. In a process for continuously separating, in a liquid phase, the components of a liquid hydrocarbon feedstream wherein at least one of said components is selectively adsorbed by contact with a solid sorbent utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent, the improvement which comprises:
   a. heating a desorbent stream containing $C_8$-$C_{18}$ paraffinic diluent and from about 10 to about 100 weight percent of a desorbent to a temperature which is at least about 5° C. higher than the operating temperature of said rectification zone;
   b. introducing said heated desorbent stream into the first section of said desorption zone;
   c. withdrawing a desorption effluent containing a selectively sorbed component from the last section of said desorption zone;
   d. cooling a portion of said desorption effluent to a temperature which is substantially identical to the operating temperature of said rectification zone;
   e. introducing said cooled portion of the desorption effluent into the first section of said rectification zone;
   f. introducing said hydrocarbon feed mixture into the first section of said sorption zone; and
   g. withdrawing a raffinate effluent containing a less sorbed component from the last section of said sorption zone.

16. The process of claim 15 wherein said liquid hydrocarbon feedstream contains an olefin having from 8 to 18 carbon atoms and a paraffin having from 8 to 18 carbon atoms.

17. The process of claim 16 wherein the desorbent employed is an olefin having from 8 to 18 carbon atoms.

18. The process of claim 15 wherein said liquid hydrocarbon feedstream contains an aromatic compound having from 6 to 12 carbon atoms and an olefin having from 8 to 16 carbon atoms.

19. The process of claim 18 wherein the desorbent employed is an aromatic compound having from 6 to 14 carbon atoms.

20. The process of claim 15 wherein said liquid hydrocarbon feedstream contains a normal olefin having from 4 to 12 carbon atoms and a branched olefin having from 4 to 12 carbon atoms.

21. The process of claim 20 wherein the desorbent employed is an alkanol having from 1 to 8 carbon atoms.

22. The process of claim 15 wherein said liquid hydrocarbon feedstream contains a cis-olefin having from 4 to 8 carbon atoms and a trans-olefin having from 4 to 8 carbon atoms.

23. The process of claim 22 wherein the desorbent employed is an olefin having from 8 to 18 carbon atoms.

24. The process of claim 15 wherein said liquid hydrocarbon feedstream contains a diolefin having from 4 to 12 carbon atoms and a monoolefin having from 4 to 12 carbon atoms.

25. The process of claim 24 wherein the desorbent employed is a diolefin having from 4 to 12 carbon atoms.

26. The process of claim 15 wherein said liquid hydrocarbon feedstream contains an acyclic unsaturated hydrocarbon having from 5 to 15 carbon atoms and a cyclic unsaturated hydrocarbon having from 5 to 15 carbon atoms.

27. The process of claim 26 wherein the desorbent employed is an aromatic compound having from 6 to 10 carbon atoms.

28. In a process for continuously separating, in a liquid phase, the components of a liquid hydrocarbon feedstream containing an olefin having from 8 to 18 carbon atoms and a paraffin having from 8 to 18 carbon atoms wherein said olefin is selectively adsorbed by contact with a solid sorbent utilizing a simulated countercurrent flow system wherein liquid streams are allowed to flow downward through a desorption zone, a rectification zone, a rectification zone and a sorption zone, each zone being serially and circularly interconnected and divided into a plurality of serially interconnected sections, each section being packed with a mass of said solid sorbent, the improvement which comprises:

a. introducing a first desorbent stream containing a $C_8$-$C_{18}$ paraffinic diluent and from about 40 to about 100 weight percent of an olefinic desorbent having from 8 to 18 carbon atoms into the first section of said desorption zone;

b. withdrawing a desorption effluent containing the olefinic component of said feedstream from the last section of said desorption zone;

c. introducing a second desorbent stream containing said paraffinic diluent and from about 15 to about 60 weight percent of said olefinic desorbent into the first section of said rectification zone;

d. introducing said hydrocarbon feedstream into the first section of said sorption zone;

e. withdrawing a raffinate effluent containing the paraffinic component of said feedstream from the last section of said sorption zone; and f. wherein the concentration of said olefinic desorbent present in the first desorbent stream is higher than the concentration of said olefinic desorbent present in the second desorbent stream by at least 20 weight percent.

29. The process of claim 28 wherein the first desorbent stream employed in step (a) is heated, before it is introduced into the first section of said desorption zone, to a temperature higher than the temperature of the second desorbent stream employed in step (c).

30. The process of claim 28 wherein said solid sorbent is a crystalline aluminosilicate selected from the group consisting of zeolites substituted with Group IA, Group IB, Group IIA and Group IIB metals.

31. The process of claim 30 wherein said solid sorbent is a crystalline aluminosilicate selected from the group consisting of sodium substituted zeolite X, sodium substituted zeolite Y, copper substituted zeolite X, copper substituted zeolite Y, cadmium substituted zeolite X, cadmium substituted zeolite Y, strontium substituted zeolite X, strontium substituted zeolite Y and potassium substituted zeolite Y.

32. The process of claim 28 wherein the first desorbent stream employed in step (a) contains said olefinic desorbent in an amount ranging from about 50 to about 90 weight percent and the second desorbent stream employed in step (b) contains said olefinic desorbent in an amount ranging from about 20 to about 50 weight percent.

33. The process of claim 28 wherein the olefinic component of said feedstream withdrawn in step (b) is butene-2 and the paraffinic component of said feedstream withdrawn in step (e) is butane.

34. The process of claim 33 wherein the first desorbent stream employed in step (a) contains about 90 weight percent of octene and about 10 weight percent of octane and the second desorbent stream employed in step (c) contains about 30 weight percent of octene and about 70 weight percent of octane.

35. The process of claim 34 wherein the solid sorbent employed is a crystalline aluminosilicate selected from the group consisting of copper substituted zeolite X and cadmium substituted zeolite X.

* * * * *